(12) United States Patent
Buszman et al.

(10) Patent No.: US 12,156,808 B2
(45) Date of Patent: Dec. 3, 2024

(54) METHOD OF FORMING PREFABRICATED UNITS USED IN PRODUCTION OF SYSTEMS OF PROSTHETIC AORTIC VALVE TRANSCATHETER IMPLANTATION AND PROSTHETIC AORTIC VALVE PREFABRICATED UNIT

(71) Applicants: AMERICAN HEART OF POLAND S.A., Ustroń (PL); CENTRUM MATERIAŁÓW POLIMEROWYCH I WĘGLOWYCH POLSKIEJ AKADEMII NAUK, Zabrze (PL); POLITECHNIKA ŚLĄSKA WYDZIAŁMECHANICZNY TECHNOLOGICZNY, Gliwice (PL); ŚLĄSKIE CENTRUM CHORÓB SERCA W ZABRZU, Zabrze (PL); ZAKŁAD DOŚWAIDCZALNY INSTYTUTU ZOOTECHNIKI PIB GRODZIEC ŚLĄSKI SP. Z O.O., Świętoszówka (PL); INNOVATIONS FOR HEART AND VESSELS SP. Z O.O., Tychy (PL); HEART TEAM SP. Z O.O., Warsaw (PL)

(72) Inventors: Pawel Buszman, Katowice (PL); Piotr Dobrzynski, Zabrze (PL); Janusz Kasperczyk, Katowice (PL); Michal Sobota, Czestochowa (PL); Katarzyna Jelonek, Czestochowa (PL); Jakub Wlodarczyk, Poronin (PL); Mateusz Stojko, Laziska Gorne (PL); Mariusz Pawlak, Zabrze (PL); Wojciech Klein, Knurow (PL); Jacek Gnilka, Gliwice (PL); Arkadiusz Mezyk, Gliwice (PL); Marian Zembala, Tarnowskie Gory (PL); Michal Zembala, Zbroslawice (PL); Joanna Sliwka, Zabrze (PL); Krzysztof Milewski, Katowice (PL); Piotr Buszman, Katowice (PL); Piotr Hirnle, Warsaw (PL); Jerzy Nozynski, Zabrze (PL)

(73) Assignee: Innovations for Heart and Vessels Sp. z o.o., Katowice (PL)

( * ) Notice: Subject to any disclaimer, the term of this patent is extended or adjusted under 35 U.S.C. 154(b) by 933 days.

(21) Appl. No.: 17/262,526

(22) PCT Filed: Jul. 26, 2018

(86) PCT No.: PCT/PL2018/050040
§ 371 (c)(1),
(2) Date: Jan. 22, 2021

(87) PCT Pub. No.: WO2020/022916
PCT Pub. Date: Jan. 30, 2020

(65) Prior Publication Data
US 2021/0290380 A1     Sep. 23, 2021

(30) Foreign Application Priority Data
Jul. 24, 2018   (PL) .......................... 426434

(51) Int. Cl.
*A61F 2/86*    (2013.01)
*A61F 2/24*    (2006.01)
(Continued)

(52) U.S. Cl.
CPC .......... *A61F 2/2415* (2013.01); *A61F 2/2418* (2013.01); *A61L 27/045* (2013.01);
(Continued)

(58) Field of Classification Search
CPC ........ A61F 2/2415; A61F 2/2418; A61F 2/86; A61F 2240/001; A61L 27/045;
(Continued)

(56) References Cited

U.S. PATENT DOCUMENTS

| 5,549,635 A | 8/1996 | Solar |
|---|---|---|
| 6,007,543 A | 12/1999 | Ellis et al. |

(Continued)

FOREIGN PATENT DOCUMENTS

| CN | 107592804 A | 1/2018 |
|---|---|---|
| EP | 1637176 B1 | 6/2016 |
| WO | WO2017055926 A1 | 4/2017 |

OTHER PUBLICATIONS

Saskia Julich, European Search Report in Application EP 18 92 7966, completed on Mar. 30, 2022.
(Continued)

*Primary Examiner* — Leo B Tentoni
(74) *Attorney, Agent, or Firm* — Cherskov Playnik & Gurda, LLC

(57) ABSTRACT

A method of forming prefabricated units used in production of systems of prosthetic aortic valve transcatheter implan-
(Continued)

tation and prosthetic aortic valve prefabricated unit with an non-thrombogenic smooth surface layer or with a porous fibrous layer constituting a scaffold for epithelium cell culture, intended for manufacturing TAVI system. Stents for covering and solutions of polycarbonate silicones and/or polycarbonate urethanes and/or polyurethane with average molecular weight in the range from 50 000 g/mol to 200 000 g/mol in the solvent DMAC are prepared. Initially a smooth layer of polycarbonate silicone is applied in the electrospinning machine by electrospraying with use of the solution in DMAC with the concentration of 2-8% w/w. and/or a fiber of polycarbonate urethane is applied by electrospinning on the roller with use of the solution in DMAC with the concentration of 8-20% w/w to obtain the first surface layer, with a specified speed, number of heads, thickness of capillaries, speed of movement, voltage and distance between the capillary and the roller and the specified flow of the solution on the feeding pump and after a certain time the layer covering the roller with thickness of 1-100 µm is obtained. Thereafter the inner intermediate layer of polycarbonate silicone is formed by electrospraying. When the thickness of the layer is approximately 5 to 100 µm the process is stopped and stents are placed on the formed layer and similarly like applying the former intermediate layer the application of the inner intermediate layer is continued on the whole length of the roller. Thereafter the final surface layer is applied like the first surface layer until a prefabricated unit with the polymer material thickness from 50 to 250 µm is obtained.

9 Claims, 1 Drawing Sheet

(51) Int. Cl.
| | | |
|---|---|---|
| *A61L 27/04* | (2006.01) | |
| *A61L 27/18* | (2006.01) | |
| *A61L 27/26* | (2006.01) | |
| *A61L 27/34* | (2006.01) | |
| *B29C 70/32* | (2006.01) | |
| *B29C 70/70* | (2006.01) | |
| *D01D 1/02* | (2006.01) | |
| *D01D 5/00* | (2006.01) | |
| *D01F 6/70* | (2006.01) | |
| *D01F 6/96* | (2006.01) | |
| *A61F 2/00* | (2006.01) | |
| *B29K 69/00* | (2006.01) | |
| *B29K 75/00* | (2006.01) | |
| *B29K 83/00* | (2006.01) | |
| *B29L 31/00* | (2006.01) | |

(52) U.S. Cl.
CPC ............ *A61L 27/047* (2013.01); *D01D 5/003* (2013.01); *D01D 5/0038* (2013.01); *D01D 5/0069* (2013.01); *D01D 5/0076* (2013.01); *D01D 5/0084* (2013.01); *D01F 6/70* (2013.01); *D01F 6/96* (2013.01); *A61F 2002/0081* (2013.01); *A61F 2240/001* (2013.01); *B29K 2069/00* (2013.01); *B29K 2075/00* (2013.01); *B29K 2083/00* (2013.01); *B29L 2031/7534* (2013.01); *D10B 2331/10* (2013.01); *D10B 2509/06* (2013.01)

(58) Field of Classification Search
CPC ........ A61L 27/047; A61L 27/18; A61L 27/26; A61L 27/34; B29C 70/32; B29C 70/70; B29K 2069/00; B29K 2075/00; B29K 2083/00; B29L 2031/7534; D01D 1/02; D01D 5/0038; D01D 5/0084; D01F 6/70; D01F 6/96; D10B 2331/10; D10B 2509/06
USPC ...... 264/255, 257, 258, 331.11, 331.19, 465, 264/484; 623/1.15, 2.42, 23.68, 23.7, 623/900, 901, 910
See application file for complete search history.

(56) References Cited

U.S. PATENT DOCUMENTS

| | | | |
|---|---|---|---|
| 10,080,652 B2 | 9/2018 | Backus et al. | |
| 2004/0013873 A1* | 1/2004 | Wendorff | D01D 5/0038 428/364 |
| 2008/0249608 A1* | 10/2008 | Dave | A61L 31/128 623/1.16 |
| 2011/0301696 A1* | 12/2011 | Mangiardi | D01D 5/0084 623/1.46 |
| 2016/0296351 A1 | 10/2016 | Ballard et al. | |
| 2016/0317295 A1 | 11/2016 | Jana et al. | |
| 2017/0042668 A1 | 2/2017 | O'Connor et al. | |
| 2017/0245989 A1 | 8/2017 | Bluestein et al. | |
| 2017/0333185 A1 | 11/2017 | Weber | |
| 2018/0085214 A1 | 3/2018 | Crowley et al. | |

OTHER PUBLICATIONS

Mateusz Kachel et al., State-of-the-art of Transcatheter Treatment of Aortic Valve Stenosis and the Overview of the InFlow Project Aiming at Developing the first Polish TAVI System, Cardiology Journal 2017, pp. 685-694, vol. 24, No. 6. Published Dec. 29, 2017 in Poland.
Visegrad Patent Institute, International Search Report for Application PCT/PL2018/050040, dated Apr. 23, 2019.

* cited by examiner

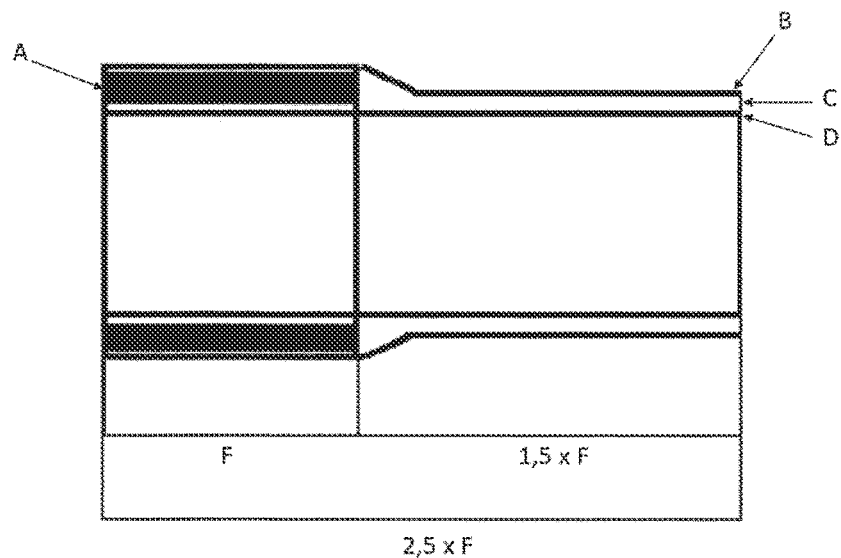

METHOD OF FORMING PREFABRICATED UNITS USED IN PRODUCTION OF SYSTEMS OF PROSTHETIC AORTIC VALVE TRANSCATHETER IMPLANTATION AND PROSTHETIC AORTIC VALVE PREFABRICATED UNIT

The invention relates to the method of processing polyurethane polymers, polyurethane carbonate polymers and polycarbonate silicone polymers and to the prosthetic aortic heart valve prefabricated unit which enables achieving prefabricated units of composite structure, used in the production of systems of prosthetic aortic valve transcatheter implantation, comprising aortic valve leaflets and a stent, with simultaneous manufacturing of the required sealing of the space between the stent and the aorta.

The method of forming, according to the invention, allows to produce the element consisting of a polymer multi-layer flexible cuff directly integrated with the metal stent in a single-step process with use of the technique of electrospinning. Thickening of the cuff wall in the place of integration which is obtained according to the method allows to strengthen and increase fatigue strength of the flexible part and it simultaneously seals the space between the aorta and the implanted stent with the valve. The other part of the cuff, with selected gradiently decreasing wall thickness, is prepared to be easily formed into the valve leaflets during further processing.

In currently produced systems of Transcatheter Aortic Valve Implantation (TAVI) or Transcatheter Aortic Valve Replacement (TAVR) components constituting the system (leaflets, sealing between the aorta and the stent) are formed separately, thereafter they are connected with the stent by sewing. The material used in prosthetic synthetic heart valves implanted with use of a method involving opening the chest of the patient as well as with use of TAVI in most cases is made of polyurethane (PU) due to its proper mechanical properties and biocompatibility. Polyurethane polymers (PU) comprise a big class of elastomers of various chemical structures, physical properties and degradation profiles. Taking into consideration the broad spectrum of properties and easy manner of manufacturing, PU are among synthetic polymers most widely used for biomedical purposes. These materials enable growth of plurality of cells (vascular cells, myofibroblasts, endothelium cells) and secretion of extracellular matrix protein (ECM) [N. Thierfelder, F. Koenig, R. Bombien, C. Fano, B. Reichart, E. Wintermantel, C. Schmitz, B. Akra, In Vitro Comparison of Novel Polyurethane Aortic Valves and Homografts After Seeding and Conditioning, Asaio J 59(3) (2013) 309-316]. However, current observations suggest the problems occurring after a long period of implantation connected with issues such as the material degradation [A. G. Kidane, G. Burriesci, M. Edirisinghe, H. Ghanbari, P. Bonhoeffer, A. M. Seifalian, A novel nanocomposite polymer for development of synthetic heart valve leaflets, Acta Biomater 5(7) (2009) 2409-2417]. In the period of the recent 10-15 years a significant progress in improving biostability of polyurethanes has been achieved. However, manufacturing PU with appropriate hemocompatibility, calcification resistance and biostabilty for long-lasting cardiological usages is still a challenge and further modification of polyurethanes is necessary. So far the materials used for manufacturing a synthetic prosthetic heart valve have included polycarbonateurethane [S. H. Daebritz, J. S. Sachweh, B. Hermanns, B. Fausten, A. Franke, J. Groetzner, B. Klosterhalfen, B. J. Messmer, Introduction of a flexible polymeric heart valve prosthesis with special design for mitralposition, Circulation 108(10) (2003) 134-139], polyester urethane [T. Courtney, M. S. Sacks, J. Stankus, J. Guan, W. R. Wagner, Design and analysis of tissue engineering scaffolds that mimic soft tissue mechanical anisotropy, Biomaterials 27(19) (2006) 3631-3638; R. Fan, A. S. Bayoumi, P. Chen, C. M. Hobson, W. R. Wagner, J. E. Mayer, M. S. Sacks, Optimal elastomeric scaffold leaflet shape for pulmonary heart valve leaflet replacement, J Biomech 46(4) (2013) 662-669. C. M. Hobson, N. J. Amoroso, R. Amini, E. Ungchusri, Y. Hong, A. D'Amore, M. S. Sacks, W. R. Wagner, Fabrication of elastomeric scaffolds with curvilinear fibrous structures for heart valve leaflet engineering, J Biomed Mater Res A 103(9) (2015) 3101-3106], nanocomposites obtained from polyhedral oligomeric silsesquioxanes and polycarbonate urethane [A. G. Kidane, G. Burriesci, M. Edirisinghe, H. Ghanbari, P. Bonhoeffer, A. M. Seifalian, A novel nanocomposite polymer for development of synthetic heart valve leaflets, Acta Biomater 5(7) (2009) 2409-2417]; polycarbonate urethane with poly(ethyl oxide) or polycaprolactone [7] N. J. Amoroso, A. D'Amore, Y. Hong, C. P. Rivera, M. S. Sacks, W. R. Wagner, Microstructural manipulation of electrospun scaffolds for specific bending stiffness for heart valve tissue engineering, Acta Biomater 8(12) (2012) 4268-4277. Polyester urethane are characterized by higher hydrolytic stability in comparison to polyurethanes and of mechanical resistance. However, they are prone to oxidative degradation of soft segments [P. Zilla, J. Brink, P. Human, D. Bezuidenhout, Prosthetic heart valves: Catering for the few, Biomaterials 29(4) (2008) 385-406]. Polycarbonate urethanes are in turn characterized by proper mechanical properties, flexibility and biostability in short-term in vitro and in vivo tests. The obstacle for their clinical use is thrombosis and hydrolytic instability observed in long-term testing. [P. Zilla, J. Brink, P. Human, D. Bezuidenhout, Prosthetic heart valves: Catering for the few, Biomaterials 29(4) (2008) 385-406]. Adding silicone to Polyurethanes, polycarbonate urethanes and polyester urethanes improves their mechanical properties and biostability. A crucial stage of manufacturing prosthetic heart valves apart from choosing a proper material is manufacturing stage, in which choice of technology of forming the material determines the final properties of the product as well as its price (number of hours of the prosthetic valve manufacturing)

The solutions known from the patent description US2017245989 in which the technology used allows to obtain the gradient of cross-section of the valve leaflet, which improves proper closing of the valve. The production solutions known from the patent description US2018085214 involve producing leaflets from a multi-layer material, which allows to obtain precise mechanical properties for applied symmetry of the leaflets. Both methods of forming leaflets involve the technique of electrospinning from polymer solutions, which proved to be successful. The same technique is used for production of sealing between the stent and the aorta. [CN107592804, US2017042668]. Production with use of the electrospinning technique allows to form a final layer of the leaflets or to form the whole leaflet in the form of fibre material—a scaffold for cell culture which will form a biological prosthetic heart valve [US2016317295].

So far in the literature, there have been no reports on a one-stage method of manufacturing a multilayer heart valve sealing integrated with a stent which changes into the material of valve leaflets with the gradient thinning of the wall cross-section without losing continuity of the material. This sealing, and the valve leaflets material are made of biocompatible and biostable polymers favourably from the group of aromatic polyurethanes, polycarbonate urethanes or polycarbonate and polycarbonate silicones.

The invention relates to the method of a one-stage manufacturing of the prosthetic heart valve and the sealing, with simultaneous fitting these elements on the stent, which simplifies the currently used technology of production TAVI systems, at the same time improving their reliability. Nowadays the technological solutions used for production of a prosthetic heart valve for TAVI systems involve the stage of connecting individual elements of the system, most commonly by sewing. Such operation requires high precision from people who manually sew leaflets and connect the sealing with the stent. Undoubtedly, it is a significant drawback taking into consideration effort and time required by this operation. Moreover, there is a high probability of occurrence of product defects and a high probability of occurrence of a human mistake. There is also a likelihood of damage of the sealing material and leaflets. It is a very costly stage of the production process due to manual work involved on the one hand and due to a very detailed quality control of the manufactured products after this operation on the other hand.

The invention relates to the manner which is characterized by the fact that multilayer materials are manufactured by electrospinning in the form of a polymer cuff permanently integrated with the stent. The prefabricated unit which is produced allows to simplify and reduce the range of manual work during the final stage of valve leaflets forming. Additionally, a seamless connection of the stent with nano-fibre with the continuous layer allows to reduce the final profile of the guiding system, thanks to which a catheter with a smaller diameter may be used. Use in the process of manufacturing TAVI system of a prefabricated unit made of biocompatible, hemocompatible, stable polymers, favourably from the group of aromatic polycarbonate urethanes and polycarbonate silicones with a layer nano-fibre, placed seamlessly on the stent formed according to the invention description, allows to obtain the material which is hemocompatible, dimensionally stable, with high flexibility and improved fatigue resistance (sensitive points which weaken the construction of such implant are the places of sewing, where disintegration of fibre appears).

The invention relates to the method which is characterized by the fact that the polymer or the polymer mixture from the group of biocompatible, hemocompatible and biostable polymers, favourably from the group of aromatic polyurethanes, polycarbonate urethanes and polycarbonate silicones with average molecular weight in the range from 50 000 g/mol to 200 000 g/mol favourably 130 000 g/mol is dissolved in a solvent favourably with low vapour pressure, favourably NN-dimethylacetamide (DMAC) or NN-dimethyloformamide (DMF). The concentrations of solutions used in this method during forming the fibre from 1% (w/w) to 20% w/w, favourably 18% by weight. In case of forming outer monolithic layers by electrospraying the concentration of the solution is lower by 10% than the concentration from which the fibres are formed. The cuff integrated with the stent is formed in the chamber of the electrospinning machine on the roller with the diameter of 18 mm to 30 mm, the size ultimately connected with the valve diameter, while the roller diameter should be smaller by 1 mm in comparison to the nominal valve diameter. The beneficial roller diameter—22 mm in case of the ultimate valve diameter 23 mm. In the variant of obtaining the material with constant thickness, the shoulder of the electrospraying and/or electrospinning head is movable. The speed of movement from 10 to 100 mm/s favourably 40 mm/s, however when the thickness gradient of the material on the length of the pre-fabricated unit is of importance, the head is fitted at a right angle over the place of the stent mounting. Due to diversity of the surface layers structure of the fibre forming the cuff which are responsible for biocompatibility and non-thrombogenicity of the material, whose thickness and morphology are shaped by the selection of ingredients and by the operating concentration of the solutions of polycarbonate urethane (table 2) or polycarbonate silicone (table 3), as well as the changes of processing parameters used in electrospinning. The invention involves two solutions. The first solution (Table 1) consists in leaving the final surface layer in the form of nano-fibres, which can constitute the scaffold on which the endothelial cells deposit. In the other solution the final surface layer is shaped in the smooth and impermeable form. The formed tight and smooth layer with a regulated process of thickness from 3 to 50 μm favourably 4.6 μm minimizes the impact of the cuff surface with blood cells, lowers the thrombogenity of this material. In both solutions during electrospinning a collector in the form of a roller with the length dependent on the stent is used. The roller should be at least 2.5× longer than the stent length. After high-gloss polishing a polymer material is being applied. The material constitutes the final layer favourably with the thickness not exceeding 3% of the optimal leaflet thickness (beneficial thickness of leaflets 100-200 μm) on the length minimally 50 mm in case of the stent for consolidation not longer than 20 mm. Applied solutions, favourably the solutions of polycarbonate silicones with average molecular weight of 70 000 g/mol in DMAC and/or the solutions of polycarbonate urethanes with average molecular weight of 200 000 g/mol in DMAC (Mw=200000) in DMAC. Another layer is applied with use of one head for one type of morphology or with use of a double head (a head for electrospraying and a head for electrospinning) powered by two solutions which allows to obtain a mixed morphology. Respectively the concentrations of polycarbonate urethanes (Mw=200000) for electrospraying are in the range of 1% w/w to 11% w/w favourably 5% w/w, while the concentrations of solutions for electrospinning are in the range from 10% w/w to 20% w/w favourably 18% w/w (depending on the molecular weight of the applied polymer). Favourably this layer does not exceed 40% of the thickness of the whole cross-section of the material layer. After finishing this stage the applied polymer layer on the roller will obtain the thickness from 10 to 60 μm favourably 57 μm, the metal stent is put onto the roller covered by the layer of formed composite, favourably made of chromo-cobalt alloy or nitinol, of open-work structure which allows to tighten it on the catheter thereafter. The stent is positioned so that to obtain the minimal total length of the cuff 2.5× the length of the valve stent—FIG. 1 Another layer is the continuation of the former layer which is applied by electrospinning (the solution of polycarbonate urethanes is in the range of the concentration from 10% w/w to 20% w/w favourably 18%) and/or electrospraying (the solution of polycarbonate urethanes in the range of the concentration from 1% w/w to 11% w/w favourably 8%) or electrospinning with simultaneous electrospraying (solution parameters). This manner allows to give the material increased desired flexibility and increases the durability of the stent consolidation. The composite layer which is formed this way should have the thickness in the range from 40 μm to 195 μm favourably 141 μm. The final stage of forming the prefabricated unit is forming the outer layer, similarly to the described above operation of creating the surface layer.

TABLE 1

Example of the material obtained according to
the invention - solution no 1

| Layer | Material and structure of the layer | Notes |
|---|---|---|
| 1 | aromatic polycarbonate urethane 1 (fibres) + aromatic Polycarbonate urethane 2 (electrospraying) | Inner layer, applied directly on the roller |
| 2 | aromatic polycarbonate urethane 1 (electrospraying) | |
| 3 | aromatic polycarbonate urethane 1 (fibres) + aromatic Polycarbonate 2 (electrospraying) | Layer of the same composition as the first one |

TABLE 1

Example of the material obtained according to
the invention - solution no 2A

| Layer | Material and structure of the layer | Notes |
|---|---|---|
| 1 | aromatic polycarbonate urethane 2 (electrospraying) | Inner layer, applied directly on the roller |
| 2 | aromatic polycarbonate urethane 1 (electrospraying) | Layer applied on the bearing element of the valve (steel stent) - increasing the adhesion of next layers |
| 3 | Aromatic polycarbonate urethane 1 (fibres) + aromatic polycarbonate 2 (electrospraying) | Layer of the same composition as the first one |
| 4 | aromatic polycarbonate urethane 1 (electrospraying | Outer layer - smoothing the surface of the material |

TABLE 1

Example of the material obtained according to the invention -
solution no 28

| Layer | Material and structure of the layer | Notes |
|---|---|---|
| 1 | polycarbonate silicone (electrospraying) | Inner layer, applied directly on the roller |
| 2 | aromatic polycarbonate urethane 1 (fibres): aromatic polycarbonate urethane 2 (electrospraying) | |
| 3 | aromatic polycarbonate urethane 1 (electrospraying) | Layer increasing the adhesion of next layers |
| 4 | aromatic polycarbonate urethane 1 (fibres): aromatic polycarbonate urethane 2 (electrospraying) | Layer of the same composition as point 2 |
| 5 | polycarbonate silicone (electrospraying) | Outer finishing layer - smoothing the surface of the material |

The invention relates to the method which guarantees repeatability of dimensions and mechanical parameters of the obtained prefabricated unit, provided that the constant temperature of manufacturing is maintained, favourably in the range of 16-22° C. and humidity favourably in the range of 50-60%. The choice of concentrations of polymer solutions used in the process of electrospinning and electrospraying (favourably not higher than 20% w/w) flows (favourably in the range of 0.5 to 2 ml/h) voltage (favourably to 40 kV) and the distance between electrodes (favourably in the range between 15-24 cm) depending on the molecular weight of a used polymer or the mixture of polymers. The dispersion of the fibres diameter and the quality of control of the fibre is specified with use of the technique of electron scanning microscopy.

The invention is presented in the examples of executions shown below and in the picture which illustrates the profile of the longitudinal section of the valve prefabricated unit consistent with the method of its manufacturing. A prefabricated unit is used in production of systems of prosthetic aortic valve transcatheter implantation consisting of: A) a stent integrated with the polymer material, B) a surface polymer layer favourably with the thickness of 1-100 µm. C) an inner intermediate polymer layer favourably with thickness of 5-100 µm—an in this layer the stent A is moulded, D) the surface layer favourably with thickness of 1-100 µm, F) the length of the stent

EXAMPLE 1

In order to obtain simultaneously five prefabricated units with athrombogenic smooth surface layer for manufacturing TAVI system in the form of a cuff made of nano-fibre integrated with a stent the following items were prepared: 5 stents made of the cobalt-nickel alloy with the wall thickness of 250 µm and of a tubular openwork structure with the outer diameter of 23 mm and the length of 18 mm, and solutions of polycarbonate silicone with average molecular weight of approximately 50 000 g/mol in DMAC, and solutions of polycarbonate urethanes with average molecular weight of approximately 200 000 g/mol in DMAC.

A steel roller with the diameter of 22 mm and with the length of 300 mm, with polished surface (surface roughness—14) was fitted in the electrospinning machine. The process of electrospinning was carried out in the humidity conditions of 40% and in the temperature of 16° C. At the beginning a surface layer made of polycarbonate silicone was applied on the roller by electrospraying with use of the solution in DMAC with the concentration of 2% w/w. The speed of the roller rotation was 250 rpm, a head equipped with one 23G capillary (size in G scale—Gauge) was fitted on the shoulder which cyclically moved at the speed of 40 mm/s along the roller. The difference in the potentials applied at the capillary and at the collector was 5 kV, and there was a distance between the capillary and the collector of 220 mm. The flow volume was established at 1 ml/h. After 2 hours the layer covering the roller with the thickness of approximately 4.6 µm and the length of 270 mm was obtained. Thereafter the inner intermediate layer was being formed with use of two heads simultaneously-one equipped with five capillaries 21G for electrospinning and the other equipped with one capillary 21 G for electrospraying, with use of the polycarbonate urethane solution with the concentration of 18% w/w on head 1 and the polycarbonate urethane solution with the concentration of 11% on head 2. The former parameters were retained, the speed of the roller rotation—250 rpm, the speed of the shoulder—40 mm/s and the voltage between the capillary and the roller—37 kV, the distance capillary—collector 220 mm. The flow on the pump feeding the polycarbonate urethane solution with the concentration of 18% w/w on head 1 was set in the amount of approximately 1 ml/h, and the polycarbonate urethane solution with the concentration of 11% w/w fed on head 2 in the amount of 0.1 ml/h. After the period of 7 h, when the thickness of the layer was approximately 57 µm the process was stopped in order to put 5 stents on the formed layer, positioning their location so that the distance between each of them was 30 mm. Then the operation of putting the outer intermediate layer on the whole length of the roller was continued with the flow decreased down to 0.5 ml/h and with other parameters retained. After the next 22 h manufacturing of the inner intermediate layer was finished, with the obtained thickness of approximately 83.8 µm. Afterwards the procedure of manufacturing the final surface layer was launched, with use of polycarbonate urethane solution in DMAC with the concentration of 5% weight by weight, the flow on the pump 1.5 ml/h and the head with one capillary, the other parameters of manufacturing remained unchanged. After 2 h the production process is finished with the removal of the manufactured products from the roller. The final products in the form of five prefabricated units with the polymer material thickness of 150 µm prepared for further simple processing in order to obtain a ready TAVI system were obtained, by dragging a formed cuff through the stent, and then cutting and sewing the valve leaflets and crimping the whole construction on the catheter.

EXAMPLE II

In order to obtain simultaneously five prefabricated units with athrombogenic smooth surface layer for manufacturing TAVI system in the form of a cuff made of nano-fibre integrated with a stent the following items were prepared: 5 stents made of the cobalt-nickel alloy with the wall thickness of 500 µm and of a tubular openwork design with the outer diameter of 23 mm and the length of 18 mm, and solutions of polycarbonate urethanes with average molecular weight of approximately 50 000 g/mol in DMAC.

A steel roller with the diameter of 22 mm and with the length of 300 mm, with polished surface (surface roughness –14) was fitted in the electrospinning machine. The process of electrospinning was carried out in the humidity conditions of 60% and in the temperature of 22° C. At the beginning a surface layer made of polycarbonate urethane was applied on the roller by electrospraying with use of the solution in DMAC with the concentration of 8% w/w. The speed of the roller rotation was 250 rpm, a head equipped with one 23G capillary was fitted on the shoulder which cyclically moved at the speed of 40 mm/s along the roller. The difference in the potentials applied at the capillary and at the collector was 37 kV, and there was a distance between the capillary and the collector of 220 mm. The flow volume was established at 1 ml/h. After 1.5 hours the layer covering the roller with the thickness of approximately 4.6 µm and the length of 270 mm was obtained. Afterwards the inner intermediate layer was being formed with use of two heads simultaneously—one equipped with five capillaries 21G for electrospinning and the other equipped with one capillary 21 G for electrospraying, with use of the polycarbonate urethane solution with the concentration of 18% w/w on head 1 and the polycarbonate urethane solution with the concentration of 11% on head 2. The former parameters were retained, the speed of the roller rotation—250 rpm, the speed of the shoulder—40 mm/s and the difference of potentials the capillary and the collector—37 kV, the distance capillary—collector 220 mm. The speed of administering the polycarbonate urethane solution with the concentration of 18% w/w through head 1 was set in the amount of approximately 1 ml/h, and the polycarbonate urethane solution with the concentration of 11% w/w fed through head 2 in the amount of 0.1 ml/h. After the period of 7 h, when the thickness of the layer was approximately 57 µm the process was stopped in order to put 5 stents on the formed layer, positioning their location so that the distance between each of them was 30 mm. Then the operation of putting the outer intermediate layer on the whole length of the roller was continued with the flow decreased down to 0.5 ml/h and the other parameters retained. After the next 22 h manufacturing of the inner intermediate layer was finished, with the obtained thickness of approximately 83.8 µm. Thereafter the procedure of manufacturing the final surface layer was launched, with use of polycarbonate urethane solution in DMAC with the concentration of 8% weight by weight, the flow on the pump 1.5 ml/h and the head with one capillary, the other parameters of manufacturing remained unchanged. After 1.5 h the production process was finished with the removal of the manufactured products from the roller. The final products in the form of five prefabricated units with the polymer material thickness of 150 µm prepared for further simple processing in order to obtain a ready TAVI system were obtained, by dragging a formed cuff through the stent, and then cutting and sewing the valve leaflets and crimping the whole construction on the catheter.

EXAMPLE III

In order to obtain simultaneously five prefabricated units with fibre surface layer enabling introduction of epithelial cells for manufacturing the TAVI system in the form of a cuff made of nano-fibre integrated with a stent the following items were prepared: 5 stents made of the cobalt-nickel alloy with the wall thickness of 250 µm and of a tubular openwork design with the outer diameter of 23 mm and the length of 18 mm, and solutions of polycarbonate urethanes with average molecular weight of approximately 200 000 g/mol in DMAC.

A steel roller with the diameter of 22 mm and with the length of 300 mm, with polished surface (surface roughness –14) was fitted in the electrospinning machine. The process of electrospinning was carried out in the humidity conditions of 50% and in the temperature of 19° C. At the beginning a fibre layer was applied on the roller with use of two heads fitted simultaneously on the shoulder moving cyclically along the roller at the speed of 40 mm/s, one head equipped with five 28G capillaries for electrospinning and the other equipped with one 21G capillary for electrospraying, with use of the polycarbonate urethane solution with the concentration of 20% w/w on head 1 and the polycarbonate urethane solution with the concentration of 11% on head 2. The process of electrospinning was carried out with the following parameters: the speed of the roller rotation-250 rpm, the difference in the potentials applied at the capillary and at the collector-37 kV, the distance between the capillary and the collector of 220 mm. The rate of the flow of polycarbonateurethane solution with the concentration of 18% w/w through head 1 was set in the amount of approximately 1 ml/h, and the polycarbonate urethane solution with the concentration of 11% w/w fed through head 2 in the amount of 0.1 ml/h. After the period of 7 h, when the thickness of the layer was approximately 57 µm the process was stopped. Thereafter an adhesive layer was applied by the method of electrospraying with use of polycarbonate urethane solution in DMAC with the concentration of 8% w/w, the speed of the roller rotation was 250 rpm, a head equipped with one 23G capillary was fitted on the shoulder which cyclically moved at the speed of 40 mm/s along the roller. The difference in the potentials applied at the capillary and at the collector was 37 kV, and there was a distance between the capillary and the collector of 220 mm. The flow volume was established at 1 ml/h. After 3 hours the process was stopped and the film layer with thickness of 9.2 µm covering the roller with the length 270 mm was obtained. Thereafter 5 stents were put on the formed layer, positioning their location so that the distance between each of them was 30 mm. The flow was decreased down to 0.5 ml/h and the other parameters were retained. The operation of putting the layer on the whole length of the roller was continued. After the next 22 h manufacturing of the inner intermediate layer was finished, with the obtained thickness of approximately 83.8 μm. The final products in the form of five prefabricated units with the polymer material thickness of 150 μm prepared for further simple processing in order to obtain a ready TAVI system were obtained, by dragging a formed cuff through the stent, and then cutting and sewing the valve leaflets and crimping the whole construction on the catheter.

EXAMPLE IV

In order to obtain simultaneously five prefabricated units with athrombogenic smooth surface layer for manufacturing TAVI system in the form of a cuff made of nanofibre integrated with a stent the following items were prepared: 5 stents made of the cobalt-nickel alloy with the wall thickness of 250 μm and of a tubular openwork design with the outer diameter of 23 mm and the length of 18 mm, and solutions of polycarbonate urethanes with average molecular weight of approximately 200 000 g/mol in DMAC.

A steel roller with the diameter of 22 mm and with the length of 300 mm, with polished surface (surface roughness −14) was fitted in the electrospinning machine. The process of electrospinning was carried out in the humidity conditions of 50% and in the temperature of 19° C. At the beginning a surface layer made of polycarbonate urethane was applied on the roller by electrospraying with use of the solution in DMAC with the concentration of 8% w/w. The speed of the roller rotation was 250 rpm, a head equipped with one 23G capillary was fitted on the shoulder which cyclically moved at the speed of 40 mm/s along the roller. The difference in the potentials applied at the capillary and at the collector-50 kV, and there was a distance between the capillary and the collector of 220 mm. The flow volume was established at 1 ml/h. After 1.5 hours the layer covering the roller with the thickness of approximately 4.6 μm and the length of 270 mm was obtained. Thereafter the inner intermediate layer was being formed with use of two heads simultaneously. One equipped with five capillaries 21G for electrospinning and the other equipped with one capillary 21 G for electrospraying, with use of the polycarbonate urethane solution with the concentration of 18% w/w on head 1 and the polycarbonate urethane solution with the concentration of 11% w/w on head 2. The former parameters were retained, the speed of the roller rotation-250 rpm, the speed of the shoulder—40 mm/s and the difference of potentials applied-37 kV, the distance capillary—collector 220 mm. The speed of feeding the polycarbonate urethane solution with the concentration of 18% w/w on head 1 was set in the amount of approximately 1 ml/h, and the polycarbonate urethane solution with the concentration of 11% w/w fed on head 2 in the amount of 0.1 ml/h. After the period of 7 h, when the thickness of the layer was approximately 57 μm the process was stopped in order to put 5 stents on the formed layer, positioning their location so that the distance between each of them was 30 mm. Thereafter the operation of putting the outer intermediate layer on the whole length of the roller was continued with the flow decreased down to 0.5 ml/h and with other parameters retained. After the next 35 h manufacturing of the inner intermediate layer was finished, with the obtained thickness of approximately 133.8 μm. Thereafter the procedure of manufacturing the final surface layer was launched, with use of polycarbonate urethane solution in DMAC with the concentration of 8% w/w the flow on the pump 1.5 ml/h and the head with one capillary, the other parameters of manufacturing remained unchanged. After 1.5 h the production process was finished with the removal of the manufactured products from the roller. The final products in the form of five prefabricated units with the polymer material thickness of 200 μm prepared for further simple processing in order to obtain a ready TAVI system were obtained, by dragging a formed cuff through the stent, and then cutting and sewing the valve leaflets and crimping the whole construction on the catheter.

EXAMPLE V

In order to obtain simultaneously five prefabricated units with athrombogenic smooth surface layer for manufacturing TAVI system in the form of a cuff made of nanofibre integrated with a stent the following items were prepared: 5 stents made of the cobalt-nickel alloy with the wall thickness of 250 μm and of a tubular openwork design with the outer diameter of 23 mm and the length of 18 mm, and solutions of polycarbonate silicone with average molecular weight of approximately 50 000 g/molin DMAC, and solutions of polycarbonate urethanes with average molecular weight of approximately 200 000 g/mol in DMAC.

A steel roller with the diameter of 22 mm and with the length of 300 mm, with polished surface (surface roughness −14) was fitted in the electrospinning machine. The process of electrospinning was carried out in the humidity conditions of 50% and in the temperature of 19° C. At the beginning a surface layer made of polycarbonate silicone was applied on the roller by electrospraying with use of the solution in DMAC with the concentration of 8% w/w. The speed of the roller rotation was 250 rpm, a head equipped with one 23G capillary was fitted on the shoulder which cyclically moved at the speed of 40 mm/s along the roller. The difference in the potentials applied was 37 kV, and there was a distance between the capillary and the collector of 220 mm. The flow volume was established at 1 ml/h. After 1.5 hours the layer covering the roller with the thickness of approximately 4.6 μm and the length of 270 mm was obtained. Thereafter the inner intermediate layer was being formed with use of two heads simultaneously. One equipped with five capillaries 21G for electrospinning and the other equipped with one capillary 21 G for electrospraying, with use of the polycarbonate urethane solution with the concentration of 18% w/w on head 1 and the polycarbonate urethane solution with the concentration of 11% on head 2. The former parameters were retained, the speed of the roller rotation—250 rpm, the speed of the shoulder—40 mm/s and the voltage between the capillary and the roller—37 kV, the distance capillary—collector 220 mm. The flow on the pump feeding the polycarbonate urethane solution with the concentration of 18% w/w on head 1 was set in the amount of approximately 1 ml/h, and the polycarbonate urethane solution with the concentration of 11% w/w fed on head 2 in the amount of 0.1 ml/h. After the period of 1 h, when the thickness of the layer was approximately 7 μm the process was stopped in order to put 5 stents on the formed layer, positioning their location so that the distance between each of them was 30 mm. The flow was decreased down to 0.5 ml/h. The other parameters retained. Thereafter the operation of putting the outer intermediate layer on the whole length of the roller was continued. After the next 13 h manufacturing of the inner intermediate layer was finished, with the obtained thickness of approximately 33 μm. Thereafter the procedure of manufacturing the final surface layer was launched, with use of polycarbonate urethane solution in DMAC with the concentration of 8% w/w, the flow on the pump 1.5 ml/h and the head with one capillary. The other parameters of manufacturing remained unchanged. After 1.5 h the production process is finished with the removal of the manufactured products from the roller. The final products in the form of five prefabricated units with the polymer material thickness of 50 μm prepared for further simple processing in order to obtain a ready TAVI system were obtained, by dragging a formed cuff through the stent, and then cutting and sewing the valve leaflets and crimping the whole construction on the catheter.

EXAMPLE VI

In order to obtain simultaneously five prefabricated units with athrombogenic smooth surface layer for manufacturing TAVI system in the form of a cuff made of nanofibre with the cross-section gradient change integrated with a stent the following items were prepared: 1 stent made of the cobalt-nickel alloy with the wall thickness of 250 μm and of a tubular openwork design with the outer diameter of 23 mm and the length of 18 mm, and solutions of polycarbonate urethanes with average molecular weight of approximately 200 000 g/mol in DMAC.

A steel roller with the diameter of 22 mm and with the length of 100 mm, with polished surface (surface roughness −14) was fitted in the electrospinning machine. The process of electrospinning was carried out in the humidity conditions of 50% and in the temperature of 19° C. At the beginning a surface layer made of polycarbonate urethane was applied on the roller by electrospraying with use of the solution in DMAC with the concentration of 8% w/w. The speed of the roller rotation was 250 rpm, a head equipped with one 23G capillary was fitted on the stationary shoulder in the place of mounting the stent on the further operations, the shoulders remains stationary till the end of manufacturing the prefabricated unit, the difference voltage between the capillary and the roller—37 KV, and there was a distance between the capillary and the collector of 220 mm. The flow volume was established at 1 ml/h. After 30 min. the layer covering the roller with the thickness of approximately 4.6 μm, in the place directly under the capillary, moving away from this place the measured thickness of a small extreme position on the roller the thickness approximately 3.4 μm and the length 100 mm. Thereafter the inner intermediate layer was being formed with use of two heads simultaneously, one equipped with five capillaries 21G for electrospinning and the other equipped with one capillary 21 G for electrospraying, with use of the polycarbonate urethane solution with the concentration of 18% w/w on head 1 and the polycarbonate urethane solution with the concentration of 11% on head 2. The former parameters were retained, the speed of the roller rotation—250 rpm, the shoulder with fitted heads remains stationary and the voltage between the capillary and the roller—50 kV, the distance capillary—collector 220 mm. The flow on the pump feeding the polycarbonate urethane solution with the concentration of 18% w/w on head 1 was set in the amount of approximately 1 ml/h, and the polycarbonate urethane solution with the concentration of 11% w/w fed on head 2 in the amount of 0.1 ml/h. After the period of 2.5 h, when the thickness of the layer was approximately 57 in the place directly under the capillary, moving away from this place the measured thickness decreases, in the extreme position on the roller the thickness was approximately 47 μm. The process was ended in order to put 1 stent n the formed layer, positioning it perpendicularly under the capillaries. Thereafter with the decreased flow down to 0.5 ml/h with the other parameters unchanged the operation of putting the inner intermediate layer on the whole length of the roller was continued. After the next 8.5 h manufacturing of the inner intermediate layer was finished, with the obtained thickness of approximately 83.8 μm in the place directly under the capillary, moving away from this place the measured thickness decreases gradually down to approximately 62.2 μm. Thereafter the procedure of manufacturing the final surface layer was launched, with use of polycarbonate urethane solution in DMAC with the concentration of 8% w/w, the flow on the pump 1.5 ml/h and the head with one capillary. The other parameters of manufacturing remained unchanged. After 30 min the production process is finished with the removal of the manufactured products from the roller. The final product in the form of a prefabricated unit—a metal stent with attached nano-fibre with the thickness of polymer material of approximately 150 μm, gradiently thinning to the final thickness of approximately 112.5 μm prepared for further simple processing in order to obtain a ready TAVI by dragging a formed cuff through the stent, and then cutting and sewing the valve leaflets and crimping the whole construction on the catheter.

The invention claimed is:

1. A method of forming prefabricated units used in production of systems of prosthetic aortic valve transcatheter implantation with a non-thrombogenic smooth surface layer or with a porous fibrous layer constituting a scaffold for epithelium cell culture, intended for manufacturing TAVI system in form of a material made of nanofiber integrated with a stent, comprising:
   preparing between 1 and 133 stents made of a cobalt-nickel alloy with a wall thickness of 150-500 μm
   providing solutions of polycarbonate silicones and/or polycarbonate urethanes and/or polyurethane with average molecular weight in range from 5000 g/mol to 200 000 g/mol in a solvent DMAC,
   providing an electrospinning machine operating with humidity conditions in range of 40-60% and in temperature in the range of 16-22° C.
   electrospraying a smooth layer of polycarbonate silicone is applied with use of the solution in DMAC with a concentration of 2-11% w/w. and/or by electrospinning polycarbonate urethane fiber is applied with use of the solution in DMAC with concentration of 8-20% w/w. onto a roller to obtain a first surface layer,
   applying specified speed, number of heads, thickness of capillaries, rotation speed, voltage and distance between each capillary and the roller, whereas flow on a pump administering the solution on the heads is set for 0.2 to 5 ml/h and after a period of 30 min to 40 ml/h forming a layer covering the roller with thickness of approximately 1-100 μm and a length of 50-6000 mm, thereafter
   forming an inner intermediate layer by electrospraying the layer of polycarbonate silicone with use of the solution in DMAC with a concentration of 2-8%/w. and/or by electrospinning the polycarbonate urethane silicone with use of the solution in DMAC with the concentration of 8-20%/w. applying specified speed, number of heads, thickness of capillaries, rotation speed, voltage and distance between each capillary and the roller, and after the period of 30 min to 40 h, when the thickness of the layer is approximately 5 to 100 μm, the forming is stopped, and
   placing the stents onto the formed layer, positioning their location so that the distance between each of them was 30 mm, and similarly to applying the inner intermediate layer,
   applying the inner intermediate layer on entire length of the roller, obtaining the thickness of approximately 5 to 100 μm after 30 min to 40 h, thereafter a final surface layer is applied similarly to the first surface layer until prefabricated units of a polymer material thickness of 50 to 250 µm is obtained.

2. The method of claim 1 wherein speed of the roller rotation is between 100 to 6000 rpm.

3. The method of claim 1, wherein the electrospinning machine is equipped with a head and/or a multi-head equipped with capillaries with the thickness of 21-28G in an amount of 1 to 100.

4. The method of claim 1, wherein the electrospinning machine head is fitted on a shoulder which moves cyclically at the speed of 40 mm/s along the roller foe a prefabricated unit with a constant material thickness and/or with a stationary shoulder for prefabricated units with gradient thinning of material cross-section.

5. The method of claim 1, wherein a gradient of difference in the material thickness with gradient thinning of polymer material cross-section is 10 µm for each centimeter of the longitudinal dimension of the material.

6. The method of claim 1, wherein the voltage between each capillary and the roller was applied in the range of 5 kV-50 kV, maintaining the distance between them from 30 to 500 mm.

7. The method of claim 1, further comprising a steel roller with a diameter in the range of from 19 mm to 25 mm and with the length of from 50 mm to 6000 mm and with a polished surface with surface roughness of 14.

8. A prefabricated unit used in production of systems of prosthetic aortic valve transcatheter implantation with a non-throbogenic smooth surface layer or with a porous fibrous layer constituting a scaffold for epithelium cell culture, intended for manufacturing TAVI system in form of a material made of nanofiber integrated with a stent, comprising a first surface layer made of polycarbonate silicone and/or polycarbonate urethane and/or polyurethane with average molecular weight from 50 000 g/mol to 200000 g/mol with thickness of 1-100 µm, formed by electrospraying or electrospinning inner intermediate layer with thickness from 5 to 100 µm made of the first surface material is applied and in this surface stents made of cobalt-nickel with wall thickness from 150-500 µm and of tubular openwork design with an outer diameter from 20-26 mm and with a length from 10-40 mm are located, and the inner intermediate surface is covered by a final surface layer with thickness 1-100 µm made of the material of the first surface layer, obtaining a prefabricated unit of a prosthetic heart valve with a polymer material thickness from 50 to 250 µm.

9. The prefabricated unit of claim 8 wherein a cross-section of the polymer material is thinned with a thickness difference gradient of 10 µm for each centimeter of the longitudinal dimension of material.

* * * * *